(12) United States Patent
Basu

(10) Patent No.: US 11,330,993 B2
(45) Date of Patent: *May 17, 2022

(54) SENSOR AND METHOD FOR CONTINUOUS HEALTH MONITORING

(71) Applicant: Wayne State University, Detroit, MI (US)

(72) Inventor: Amar S. Basu, Novi, MI (US)

(73) Assignee: Wayne State University, Detroit, MI (US)

(*) Notice: Subject to any disclaimer, the term of this patent is extended or adjusted under 35 U.S.C. 154(b) by 441 days.

This patent is subject to a terminal disclaimer.

(21) Appl. No.: 16/284,329

(22) Filed: Feb. 25, 2019

(65) Prior Publication Data

US 2019/0183364 A1 Jun. 20, 2019

Related U.S. Application Data

(63) Continuation of application No. 14/388,018, filed as application No. PCT/US2013/033980 on Mar. 27, 2013, now Pat. No. 10,219,709.

(Continued)

(51) Int. Cl.
*A61B 5/1455* (2006.01)
*A61B 5/024* (2006.01)
(Continued)

(52) U.S. Cl.
CPC ...... *A61B 5/02433* (2013.01); *A61B 5/02007* (2013.01); *A61B 5/0285* (2013.01);
(Continued)

(58) Field of Classification Search
None
See application file for complete search history.

(56) References Cited

U.S. PATENT DOCUMENTS

| 4,889,132 A | 12/1989 | Hutcheson et al. |
| 5,964,701 A | 10/1999 | Asada et al. |

(Continued)

OTHER PUBLICATIONS

Augustyniak, P., "Wearable wireless heart rate monitor for continuous long-term variability studies", *J Electrocardiol.*, 44(2), pp. 195-200, (Mar. 2011).

(Continued)

*Primary Examiner* — Marjan Fardanesh
(74) *Attorney, Agent, or Firm* — Fishman Stewart PLLC

(57) ABSTRACT

An optical proximity sensor assembly includes an optical proximity sensor with an IR LED emitting light having an infrared wavelength, an IR photo detector sensitive to the infrared wavelength, an optical barrier blocking direct light rays from the LED to the IR photo detector and permitting reflected light rays to reach the at least one photo detector; and an electronic integrated circuit with an amplifier for amplifying a signal detected by the photo detector, an analog to digital converter, LED drivers, noise reduction and ambient light cancellation circuitry, and a digital interface for communication with a microcontroller. The optical proximity sensor is accommodated on a wearable carrier. A single sensor may include a plurality of identical or different LEDs, a plurality of photodiodes, or both. Also, several sensors may be placed on a person's skin along a vascular path to obtain data relating to blood flow and artery stiffness.

22 Claims, 9 Drawing Sheets

Related U.S. Application Data

(60) Provisional application No. 61/616,524, filed on Mar. 28, 2012.

(51) Int. Cl.
*A61B 5/02* (2006.01)
*A61B 5/00* (2006.01)
*A61B 5/0285* (2006.01)
*A61B 5/021* (2006.01)
*A61B 5/026* (2006.01)

(52) U.S. Cl.
CPC ........ *A61B 5/02416* (2013.01); *A61B 5/1455* (2013.01); *A61B 5/14552* (2013.01); *A61B 5/6815* (2013.01); *A61B 5/6816* (2013.01); *A61B 5/6826* (2013.01); *A61B 5/6838* (2013.01); *A61B 5/6867* (2013.01); *A61B 5/7203* (2013.01); *A61B 5/002* (2013.01); *A61B 5/0261* (2013.01); *A61B 5/02125* (2013.01); *A61B 5/02427* (2013.01); *A61B 5/14551* (2013.01); *A61B 2562/0233* (2013.01); *A61B 2562/0238* (2013.01); *A61B 2562/04* (2013.01); *A61B 2562/046* (2013.01)

(56) References Cited

U.S. PATENT DOCUMENTS

| | | | |
|---|---|---|---|
| 6,277,079 B1 * | 8/2001 | Avicola | A61B 5/02433 600/502 |
| 6,330,468 B1 | 12/2001 | Scharf | |
| 6,533,729 B1 | 3/2003 | Khair et al. | |
| 6,898,451 B2 * | 5/2005 | Wuori | A61B 5/14532 600/310 |
| 7,117,721 B2 | 10/2006 | Neel et al. | |
| 7,771,361 B2 | 8/2010 | Bae et al. | |
| 7,822,299 B2 | 10/2010 | Borgos et al. | |
| 2007/0260130 A1 * | 11/2007 | Chin | A61B 5/6819 600/323 |
| 2008/0208009 A1 | 8/2008 | Shklarski | |
| 2009/0073461 A1 | 3/2009 | Borgos et al. | |
| 2009/0143655 A1 | 6/2009 | Shani | |
| 2009/0163783 A1 | 6/2009 | Mannheimer et al. | |
| 2009/0203972 A1 | 8/2009 | Heneghan et al. | |
| 2010/0016733 A1 | 1/2010 | Smith et al. | |
| 2011/0028814 A1 * | 2/2011 | Petersen | A61B 5/6833 600/324 |

OTHER PUBLICATIONS

Barreto, "Digital Processing of Photoplethysmographic Blood Volume Pulse (BVP) for Exercise Evaluation", *Digital Signal Processing Laboratory*, (1994).

Barreto, A., Heimer, M., and Garcia, M., "Characterization of Photoplethysmographic Blood Volume Pulse Waveforms for Exercise Evaluation", *IEEE*, pp. 220-223, (1995).

Marques, Fabio A. Ferreira, et al., "A Real Time, Wearable ECG and Blood Pressure Monitoring System", *Information Systems and Technologies (CISTI)*, (2011).

Padilla, J.M., et al., "Pulse wave velocity and digital volume pulse as indirect estimators of blood pressure: pilot study on healthy volunteers", *Cardiovasc Eng.*, 9(3), pp. 104-112, (Sep. 2009).

Tsai, W.C., et al., "Association of risk factors with increased pulse wave velocity detected by a novel method using dual-channel photoplethysmography", *Am J Hypertens*, 18(8); 1118-22 (Aug. 2005).

Wang, Lei, Lo, Benny, and Yang, Guang-Zhong, "Multichannel Reflective PPG Earpiece Sensor With Passive Motion Cancellation", IEEE Transactions on Biomedical Circuits and Systems, vol. 1 ,No. 4, pp. 235-241, (Dec. 2007).

* cited by examiner

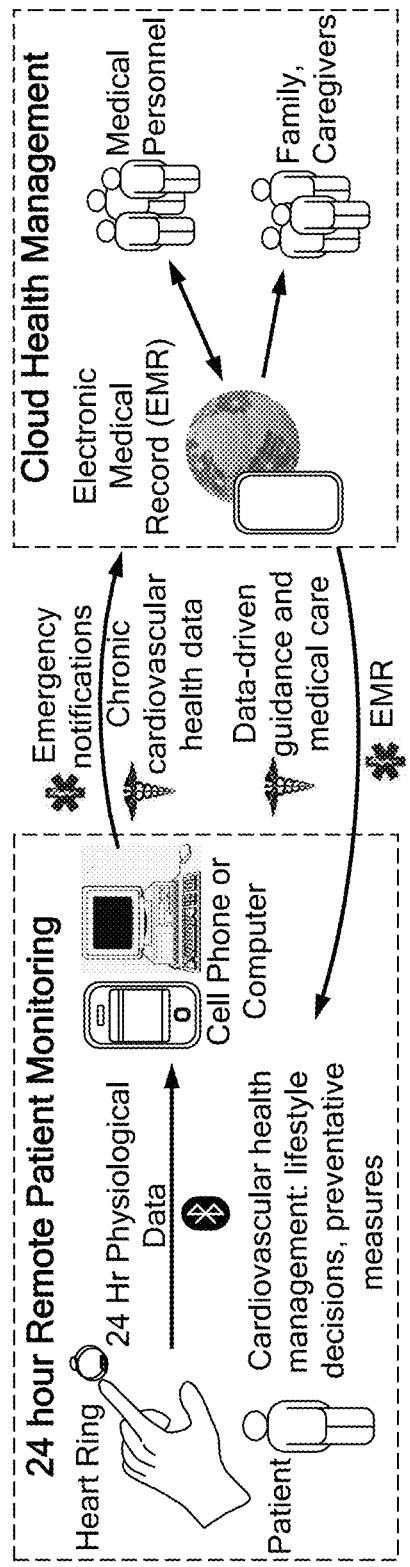
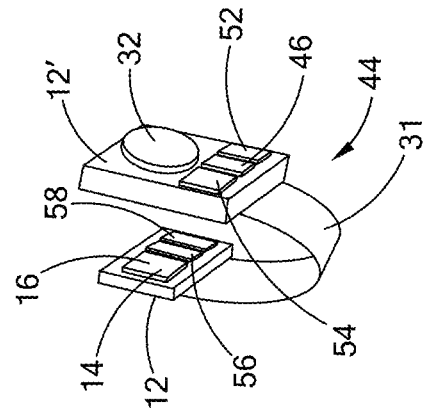
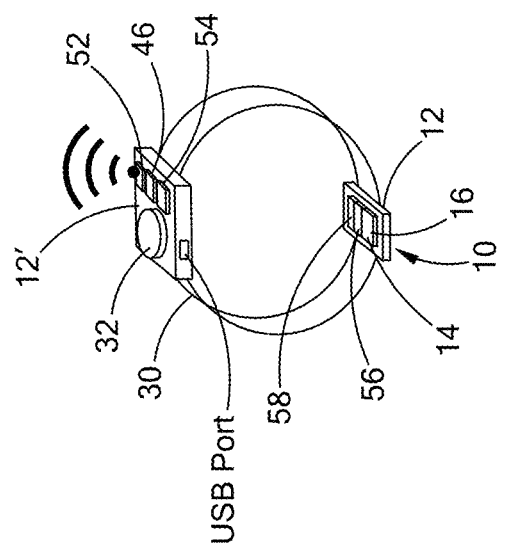
FIG. 11
FIG. 13
FIG. 12

SENSOR AND METHOD FOR CONTINUOUS HEALTH MONITORING

CROSS-REFERENCE TO RELATED APPLICATIONS

This application is a continuation of U.S. application Ser. No. 14/388,018, which is the National Phase of International Application No. PCT/US2013/033980, filed on Mar. 27, 2013, entitled "Sensor and Method for Continuous Health Monitoring," and claims the priority of U.S. Provisional Application No. 61/616,524, filed on Mar. 28, 2012, entitled "Sensor for Continuous Health Monitoring." The disclosures of the aforementioned applications are hereby included by reference in their entirety.

TECHNICAL FIELD

The present invention relates to a device, a system, and a method for vascular health monitoring of a person. More particularly, the invention relates to a sensor suitable for remote patient monitoring.

BACKGROUND OF THE INVENTION

Remote patient monitoring (RPM), also called telehealth or telemonitoring, is a growing trend in modern health care with a multi-billion dollar market. This is useful for monitoring in many chronic diseases, including cardiovascular health, chronic fatigue syndrome, depression, and related ailments, and sleep-related ailments such as insomnia or sleep apnea.

Remote patient monitoring has an important role in the management of patients at-risk for complications of cardiovascular disease.

There is an unmet need for convenient 24-hour physiological monitoring. Existing pulse oximeters and heart rate sensors typically cost more than about $80 and are in the form of chest straps, cuffs, palm-sized ambulatory sensors, or large modules clipped to the end of a finger as illustrated in FIG. 3A. Such form factors of the current technology are not well suited for 24-hour monitoring because it is expensive and/or uncomfortable to the patient. 24-hour monitoring is important because managing the subtle symptoms of chronic disease (such as heart disease, chronic fatigues syndrome, depression, etc.) relies on the ability to continuously monitor physiological parameters without placing burden to the patient. The large size, however, causes patient discomfort or limits mobility. While costs are moderate (more than about $100), it is still too expensive to be ubiquitously accepted by health care providers. Current devices also consume too much power to provide 24 hour operation.

SUMMARY OF THE INVENTION

History has shown that with many sensor technologies, the key to widespread acceptance is to enable the sensor for 'plug-and-play'. The ideal sensor should function out of the box without additional components, and it should provide a direct digital interface to a microcontroller. It should also be small, and relatively low cost (few dollars or less). The most successful example of a plug and play sensor in recent history is the accelerometer, which has seen rapid, pervasive growth in the smart phone, automotive safety, and home entertainment markets.

According to a first aspect of the invention, an optical proximity sensor assembly includes an optical proximity sensor with an IR LED emitting light having an infrared wavelength, an IR photo detector sensitive to the infrared wavelength, an optical barrier blocking direct light rays from the LED to the IR photo detector and permitting reflected light rays to reach the at least one photo detector; and an electronic integrated circuit with an amplifier for amplifying a signal detected by the photo detector, an analog to digital converter, LED drivers, noise reduction and ambient light cancellation circuitry, and a digital interface for communication with a microcontroller. The optical proximity sensor is accommodated on a wearable carrier.

According to further embodiments of the invention, a single sensor may include a plurality of identical or different LEDs, a plurality of photodiodes, or both.

Also, several sensors may be placed on a person's skin along a vascular path to obtain data relating to blood flow and artery or vascular stiffness this type of measurement is referred to as pulse wave velocity and is an indicator of cardiovascular health.

Further details and advantages of the invention become apparent in the following description of various preferred embodiments by way of the attached drawings. the drawings are included for purely illustrative purposes and are not intended to limit the scope of the present invention.

BRIEF DESCRIPTION OF THE DRAWINGS

FIG. 11: A long term concept using RPM for at-risk cardiovascular patients to actively manage their cardiovascular health;

FIG. 12: A schematic of an alternative proposed sensor system for heart rate monitoring, with parts drawn approximately to scale;

FIG. 13: A schematic of a further alternative proposed sensor system for heart rate monitoring, with parts drawn approximately to scale;

DETAILED DESCRIPTION

This invention includes new technologies for simultaneously sensing heart rate, blood pressure and pulse oximetry. These technologies can be combined in one sensor. The blood pressure may be indirectly measured using pulse wave velocity by placing several sensors in different locations along an artery. In this manner, vascular conditions can be detected, such as restricted blood flow.

In a first approach, this device utilizes electronic optical proximity sensors (OPS) 10 to sense a patient's heart rate. Optical proximity sensors, also called light beam sensors, detect distance by measuring the magnitude of light reflected from an object. Variations of OPS are widely used for non-contact distance measurement in a variety of applications. In smart phones, for example, OPS detect when a phone is placed in a pocket, triggering touch-screen locking. In factory robotics, OPS are used for motion feedback control. In many industrial and consumer applications, OPS serve as touchless switches and gesture sensing devices in personal notebooks, vending machines, sanitary dispensers, lavatories, dimming control, and video games.

Figure 1:
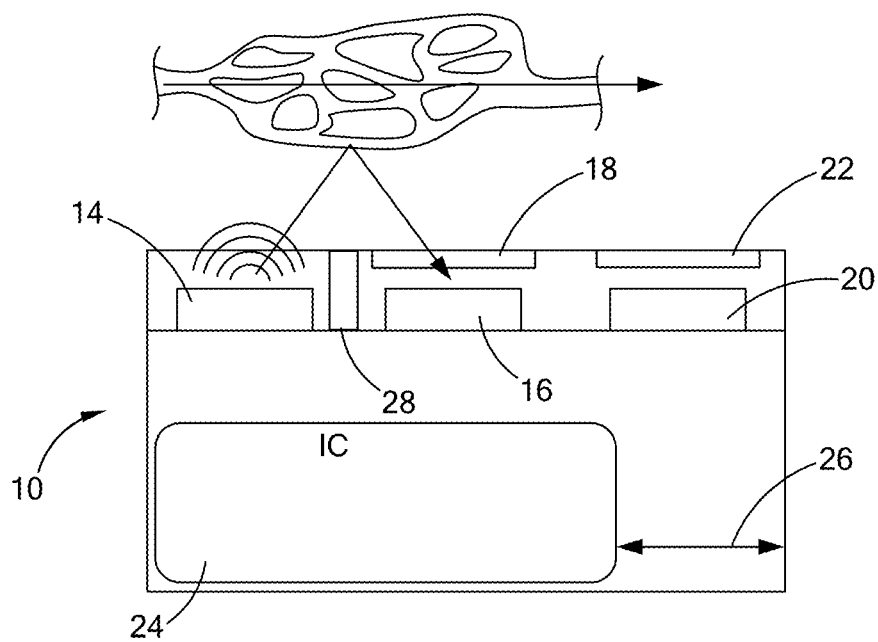
FIG. 1: Structural features of and optical proximity sensor and its use in photoplethysmography.

As, for example, shown in FIG. 1, An OPS 10 includes an infrared (IR) light emitter, such as an IR LED 14, and an integrated circuit (IC) 24 providing LED drivers modulating the infrared light emitter at a fixed or varying frequency. The drivers may also operate in a burst or low duty cycle operation where the measurement is performed quickly, and then the IR emitter is shut off to conserve power. The OPS 10 includes mixed signal circuits for amplification, signal conditioning, and digitization, i.e. analog-digital conversion, of the detected radiation. During frequency modulation, the LED 14 is pulsed at a predetermined and unique, fixed or variable, frequency. In return the detection circuitry is operated with a digital lock-in technique to detect and select the photodiode signal at the same frequency and phase as the operation of the LED driver. uses a digital lock in technique to select the photodiode signal which is at the same frequency and phase as the signal driving the LED.

The influx of ambient light can be measured during OFF phases of the LED 14. The ambient light component can then be subtracted from the photo detector signal during ON phases to provide a sensitivity offset for proper calibration. This technique being similar in concept to lock-in detection or to electronic noise cancellation, it improves the signal to noise ratio and reduces the impact of noise and ambient light.

The OPS 10 further includes an IR photodiode 16, a visible light blocking filter 18, an optical barrier 28. An optional second photodiode 20, sensitive to visible light, may serve as an ambient lights sensor (ALS), useful for ambient noise cancellation.

Figure 2:
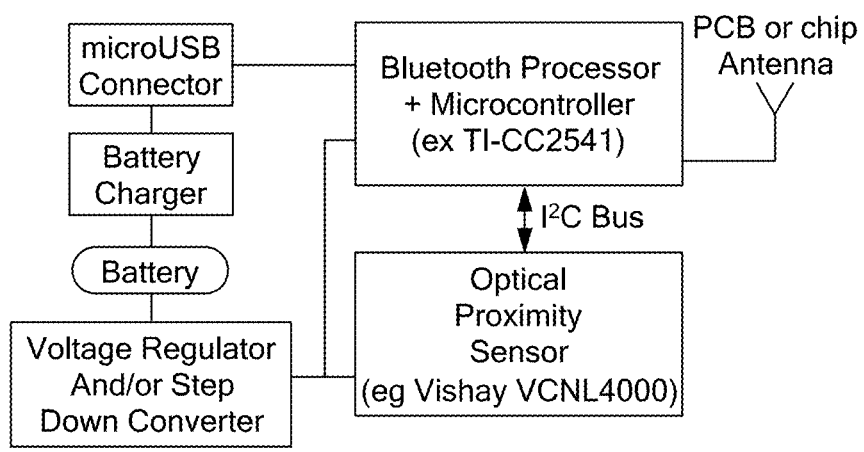
FIG. 2: An example of a circuitry of an optical proximity sensor according to the invention for monitoring the heart rate.

An IR blocking filter 22 is arranged to protect the photodiode 20 from pollution from scattered IR radiation. Integrated digital OPS 10, available recently, are highly integrated devices which include all the above components in a small, surface mount package, typically a few millimeters in size. These sensors also provide a bidirectional serial interface 26 to a microcontroller for sending data and configuring the device. Instead of or in addition to the serial interface 26, a wireless transmitter may be incorporated in the device, for example in the form of a Bluetooth® module 46, as indicated in FIG. 2.

Figure 3A:
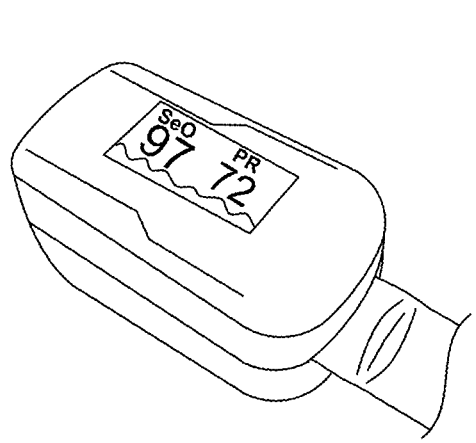
FIG. 3A One of the smallest pulse oximeters currently available
Figure 3B:
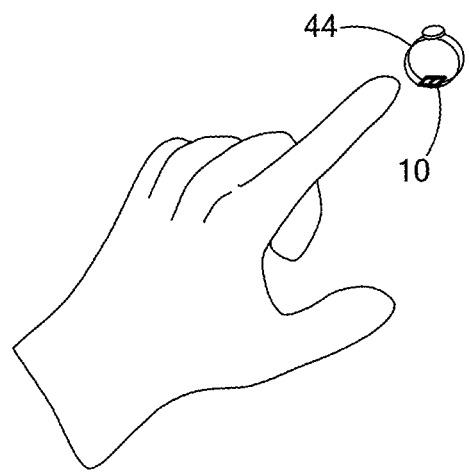
FIG. 3B: A proposed wireless, 24-hour wearable heart monitor.
Figure 3C:
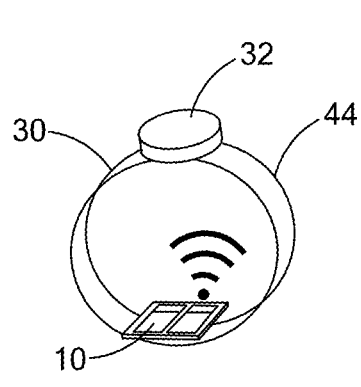
FIG. 3C: A schematic of a proposed sensor system for heart rate monitoring, with parts drawn approximately to scale.
Figure 4:
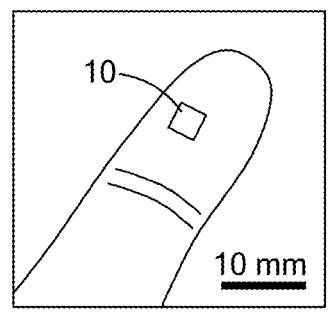
FIG. 4: An illustration of the size of a sensor according to one embodiment of the present invention suitable for placing on fingers or earlobes.

OPS 10 can provide heart rate sensing comparable to commercial reflectance photoplethysmography devices and reflectance pulse oximeters, but in a much more compact package with a printed circuit board (PCB) area less than about 16 mm$^2$ compared to typical detectors with a PCB area of 200 mm$^2$ for all the individual components. More importantly the power consumption is less than about 200 µW compared to 10 mW for conventional photoplethysmography sensors. This order of magnitude improvement makes it possible to make a 24 hour heart rate sensor integrated in a wearable carrier, and one small enough to be worn unobtrusively in on a finger, ear, etc. Due to the low power consumption, a battery 32 holding a charge for operating the OPS for at least 24 hours can be unobtrusively small. For example, FIGS. 3B and 3C show an OPS 10 integrated in wearable carrier in the form of a finger ring 44, in which the ring shape is formed by a flexible cable 30. The cable 30 connects the OPS 10 with a rechargeable battery 32 providing for a sufficient capacity for at least several hours of monitoring, preferably at least 24 hours. FIG. 4, for example, is a picture of an OPS 10 used for photoplethysmography placed on a finger tip. Although the capillary bed is smaller than the fingertip, the presence of reflective bone backing formed by the finger bone improves the reflected signal.

Figure 5:
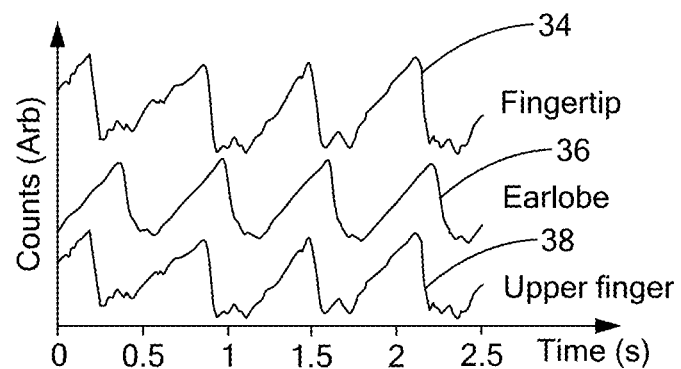
FIG. 5: Illustrative examples of heart rate measurements using a sensor according to an embodiment of the invention in different locations of a human body.

Heart rate sensing can be performed with the OPS 10 with more than one order of magnitude improvement in power compared to conventional methods. FIG. 5 illustrates pulse shapes for an OPS 10 placed in different locations on a patient's body. The top curve 34 shows a signal obtained from a OPS 10 placed on a fingertip, the second curve 36 represents an OPS 10 signal from an earlobe, and the bottom curve 38 depicts an OPS 10 signal from an upper finger. As is evident, the measurement performed on the earlobe shown in curve 36 exhibits a different shape compared to the measurements 34 and 38 performed on the finger.

Figure 6A:
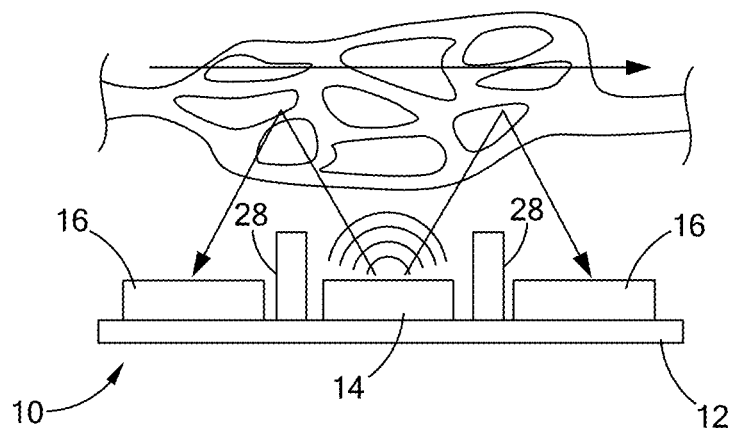
FIG. 6A: A schematic of a proposed sensor system for blood pressure monitoring with two photo detectors and two optical barriers.
Figure 6B:
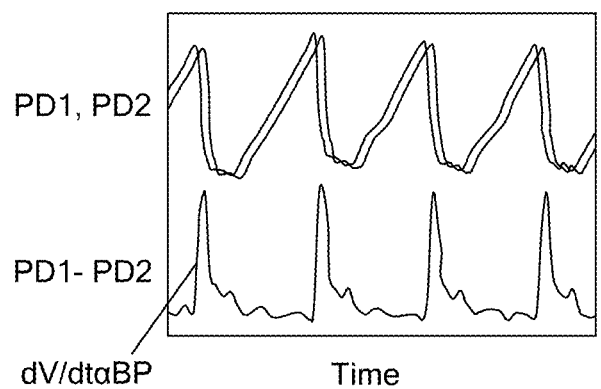
FIG. 6B: An illustrative example of determining blood pressure using a sensor according to an embodiment of the invention following the principle of FIG. 6A.
Figure 7:
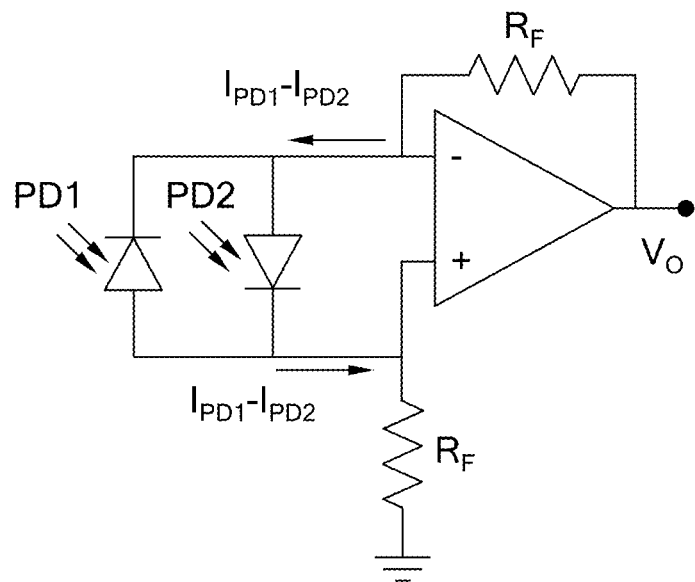
FIG. 7: A schematic of an electronic circuit for a sensor according to FIG. 6A

In a second approach, the time lag along a blood vessel system, for example, along with a change in amplitude and shape of the pulse wave can give information on restrictions and elasticity of the artery, for example due to plaque on the vessel walls. This principle is schematically depicted in FIGS. 6 and 7. An OPS 10 for detecting pulse wave velocity uses a novel sensor setup which detects how fast a pulse wave travels from one side of the sensor to the other side of the sensor (FIGS. 6A and 7). This approach can be robust to environmental noise and to drift of the sensor. Pulse wave velocity can be correlated with blood pressure. The device works in the near infrared (~950 nm) range. By putting two generally identical photodiodes 16 in two different locations on a circuit board 12 symmetrically on opposite sides of an IR LED 14, the time it takes for a pulse wave to move through the vessel can be measured as shown in the diagram of FIG. 6B. The light travels from the LED 14 through the finger to the blood vessel and tissue, where it is partially reflected. The reflected signal is sensed by each of the photodiodes 16. As a pulse of blood flows through the capillary bed, both photodiodes experience nearly identical pulse waves offset by a short transit time due to the finite velocity of the pulse wave. A difference amplifier will produce a series of pulses whose width is inversely proportional to pulse wave velocity. An illustrative electronic circuit is shown in FIG. 7.

The measured quantity is called pulse wave velocity and is correlated with blood pressure and arterial stiffness. In FIG. 6B, the top graph shows the two measurements of the photodiodes 16, and the bottom graph shows the difference of the two measurements of the upper graph. The same principle applies when two separate OPS 10 are placed in different locations of a human body, as for instance indicated in FIG. 8. Depending on the locations, the phase shift of the pulse waves may be greater.

It is notable that most of the optoelectronic components and performance specifications required for OPS 10 are the same as those used in photoplethysmography. A digital OPS 10 can serve as a high-performance, reflectance-mode photoplethysmography sensor.

Figure 3D:
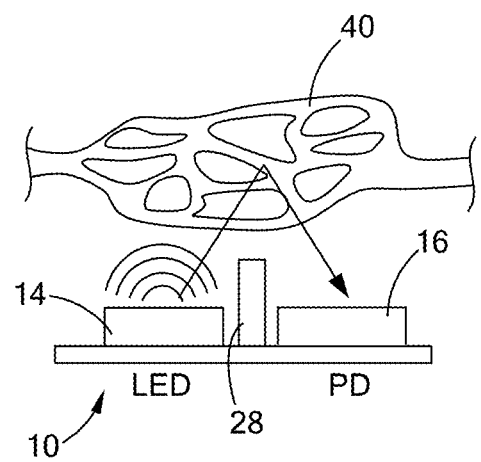
FIG. 3D: An example of an optical barrier, a component of the OPS, reducing offset and increasing accuracy.

FIGS. 3D and 1 illustrate the general working mechanism. The OPS 10 is placed in direct contact with the skin, near a capillary bed 40. Ideal locations include the fingertip, earlobe, or forehead. A protective overlay (not shown in this figure) can be added if desired. The IR LED 14 emits light into the tissue, where it experiences diffuse reflection from the tissue and capillary bed 40. This establishes a baseline reflectance signal at the IR photodiode 16. When a pressure wave propagates through the capillary bed 40, the signal falls slightly (0.5-5%) due to increased light scattering. The change is detected by an amplification and signal processing circuitry in the IC 24 embedded in the OPS 10. In the case of an earlobe or fingertip sensor, a metal backing can be placed on the opposite side of the earlobe or fingertip to improve the reflectance signal. In some embodiments, the metal backing may be provided by the battery 32.

One example of a digital OPS 10 suited for single wavelength photoplethysmography is a VCNL4000 (Vishay Semiconductor), a fully integrated digital proximity and ambient light sensor with 16-bit resolution in a 4 mm-by-4 mm leadless surface mount package. The invention, however, is not limited to the specific devices used in the described embodiments.

The OPS 10 is generally illustrated in FIG. 1 and includes an embedded 895 nm IR LED 14 and a photodiode 16 with visible light blocking filter 22. The spacing between the LED 14 and photodiode 16 is about 2 mm, resulting in a large reflectance and sensitivity. The LED 14 is embedded in a recessed region which serves as an optical barrier 28 to reduce light leakage. The embedded signal processing IC 24 handles LED modulation, current control (10-200 mA in 10 mA steps), photo detector amplification and signal conditioning, ambient light cancellation, 16-bit analog to digital conversion (ADC), and I²C bus communication. The ADC can resolve pulsation indices of 15 ppm. The LED 14 can be modulated at frequencies up to 3.1 MHz (user selectable) for electronic noise cancellation. To reduce power consumption, each measurement is completed in 75 µsec, and the LED 14 is kept off at the remainder of the measurement cycle. This allows one to use a large LED current (100 mA) while consuming less than about 200 µW power at a 100 Hz data rate. The supply voltage range is 2.5-3.6 V, which is well suited for operation from a 3V coin cell rechargeable battery 32. The IR LED 14 is placed on a separate supply to reduce the effects of digital switching noise. The I²C serial interface 26, supported by most microcontrollers, is used to transmit data and to configure the OPS 10. The cost of the component is comparatively low. Notably, the above specification is only one example of an operational OPS. For example, a 12-bit analog-to-digital conversion may be sufficient.

Multiple photoplethysmography measurements were obtained by placing the OPS 10 in firm contact with the skin at multiple locations as previously described in connection with FIG. 5. In the earlobe measurements, a metal cap was placed on the opposite side to improve the reflectance measurement. The photoplethysmography data were recorded using a Silicon Labs microcontroller directly connected to a laptop via USB. The photoplethysmography data depicted in FIG. 9 were the measurements of the different sensors take on different amplitudes, waveforms, and phases for different sensor locations. The top curve shows a measurement at the fingertip of the index finger. The second curve shows an earlobe measurement with metal backing. The third curse shows an index finger measurement, in which the sensor was applied with high pressure, the fourth measurement shows the earlobe measurement without metal backing, and the fifth curve shows the cur of the upper ring finger under low pressure. The OPS 10 were operated at a 100 Hz data rate. The proximity readings were analyzed and plotted as a function of time using technical computing software. In the described example, the software was MATLAB® by Math Works.

Several features of the digital OPS 10 make them well suited for high-performance photoplethysmography sensing:

Integrated IR LED and visible light blocking filter: In many integrated OPS 10, the emitter wavelength is in the near infrared range (850-950 nm), which is ideal for photoplethysmography. Other OPS 10 allow the designer to add any discrete LED 14' and 15, as will be later described in connection with FIGS. 14 and 15. The visible light blocking filter 14 included on some OPS 10 reduces the impact of ambient light.

Improved sensitivity due to small spacing between the photodiode (PD) and the LED: One of the challenges in reflectance mode photoplethysmography is that the majority of light emitted by the LED 14 is forward scattered (diffused) through the tissue, leaving less than about 5% backscattered to the detector. The intensity of the backscattered light, which forms a concentric ring around the excitation LED 14, falls off as the square of the distance. The limited light reduces sensitivity.

Figure 10:
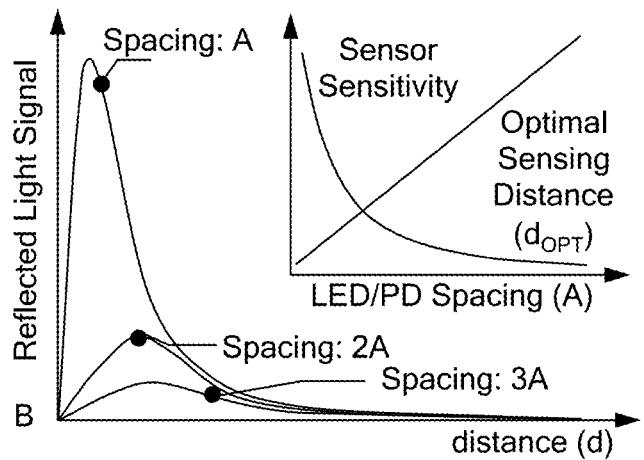
FIG. 10: Effect of LED-PD spacing on sensitivity. (A) Reflected light signal as a function of distance between sensor and OPS. (B) Illustration that, in an OPS, the spacing is less than about 2 mm and therefore well suited for monitoring.
Figure 14:
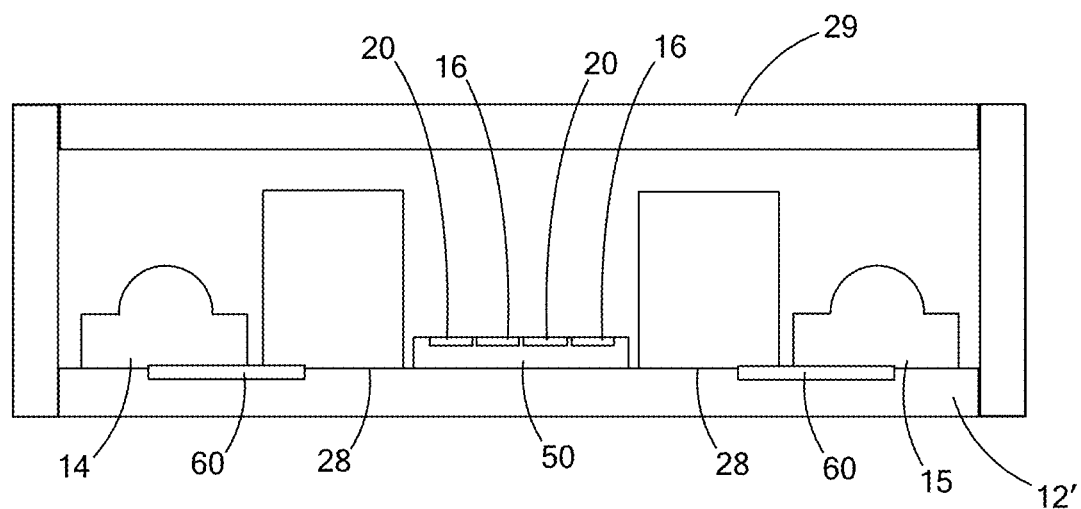
FIG. 14: A schematic of a proposed sensor system for pulse oximetry monitoring with two LEDs, one photo detector containing different photodiodes, and two optical barriers.

FIG. 14 highlights the importance of small LED-PD spacing by the example of the OPS 10 of FIG. 6A. In FIG. 10 three different values of the spacing, A, 2A, and 3A, are qualitatively compared. As the space between the LED and the photodiode is increased, the magnitude of the reflected light signal (and thus, the sensitivity) falls off as $1/A^2$ while the optimal distance $d_{OPT}$ between the LED 14 and the photodiode 16 increases proportionally with A. In a digital OPS 10, the distance between LED 14 and photodiode 16 is less than about 1-2 mm, compared to 4-5 mm in a typical photoplethysmography sensor. Therefore, the light signal is improved by a factor of about 2-25. This improves the signal-to-noise ratio by the same factor.

Optical barrier for reduced light leakage: One drawback of a small LED-PD spacing is light leakage between the two components, which increases the so-called baseline photoplethysmography signal. As shown in FIG. 3D and FIG. 6A Integrated OPS 10 include an optical barrier 28, placed between the LED 14 and the photodiode 16, which greatly reduces light leakage. The dimensions of the optical barrier 28 are important, particularly in "zero-distance detection" where the skin is in direct contact with the sensor. If the optical barrier 28 is too wide, it will block the reflectance signal completely, and if it is too thin, the baseline leakage signal could be large enough to obscure the pulsation signal. An appropriately sized optical barrier 28 helps to ensure a high signal-to-noise ratio.

High sensitivity and dynamic range due to high-resolution analog to digital conversion: A fundamental requirement in photoplethysmography sensors is the ability to detect a small pulsation superimposed on a large baseline (DC) signal. In a standard photoplethysmography sensor arrangement, the AC signal is extracted using a 0.5-5 Hz bandpass filter and additional amplifiers. Recently available digital OPS 10 incorporate a high resolution analog to digital converter (ADC), which can resolve small pulsations without additional filters. For example, a 16 bit ADC can resolve a PI as little as $\frac{1}{2}^{16}$, or 15 ppm. The advantage of this approach is that both DC and AC components of the photoplethysmography signal can be simultaneously measured. This is useful for direct measurement of the PI, and for adjusting the LED intensity to prevent saturation of the light detector. A lower resolution of at least 12 bit may even be sufficient to perform this task.

Electronic noise and offset reduction: The second function of the bandpass filter in photoplethysmography sensors is to remove high frequency noise, including 60/120 Hz noise from ambient light sources. While a 0.5-5 Hz filter can usually remove such noise, it limits the bandwidth of the photoplethysmography sensor, which makes it difficult to resolve some time dependent features of the pressure pulse. An OPS 10 uses electronic modulation to cancel noise and ambient light. The LED 14 is modulated at 1 KHz frequency or higher. The received PD signal oscillates at the same frequency, and the on-chip signal processing utilizes a bandpass or lock-in filtering scheme to remove all the other signal components. This technique effectively eliminates both high and low frequency noise without limiting the bandwidth. It also diminishes the impact of sunlight, which occurs as direct current (DC). Finally, offset can be reduced if a glass overlay (not shown) is placed between the sensor and the skin. An ambient light sensor (ALS) in the form of a visible-light photodiode 20 can also be used as a reference for additional ambient light cancelation.

Reduced power consumption via burst operation or low duty cycle operation: The IR emitting LED 14, typically being the component with the highest power consumption in a photoplethysmography sensor, is operated for short periods of time, just long enough to take a measurement, and can be 75 µs or less. The short bursts are followed by long periods of idle time. This reduces power consumption by several orders of magnitude.

Digital Interface: The OPS 10 provides a digital output on an industry standard I²C serial bus. The digital output is inherently more robust against noise than an analog interface, which is important because the photoplethysmography signal is small. In addition, the I²C serial interface 26 makes it easy to link the sensor to a microcontroller, and add multiple sensors 10 on a single bus.

Intensity control: To maximize the signal-to-noise ratio in photoplethysmography, the LED intensity should be made as large as possible without saturating the detector. In the OPS 10, the LED intensity and modulation frequencies are programmable through the serial interface. In the case of the Vishay VCNL4000, the intensity is programmable from 10-200 mA in 10 mA increments. Others (like the APDS-9190), include digital interrupts which trigger when the photo detector signal is saturated.

With its very low power consumption, the OPS 10 enables a 24-hour wireless heart rate sensor embedded on ring 44. The use of OPS 10 results in two key performance improvements.

First, as shown in FIG. 3D and FIG. 1, an optical barrier 28 placed between the LED 14 and photodiode (PD) 16 greatly reduces the offset signal by eliminating light leakage and crosstalk from the LED 14 to the photodiode 16. Second, the small distance between LED 14 and photodiode 16 improves sensitivity. One of the challenges in reflectance photoplethysmography is that the majority of light emitted by the LED 14 is forward scattered (diffused) through the tissue, leaving less than about 5% backscattered to the detector. The backscattered light, which forms a concentric ring around the excitation LED 14 falls off as $1/r^2$. In OPS 10, the distance between LED 14 and detector is less than about 1 mm, whereas traditional reflectance pulse sensors require 4-5 mm. Thus, sensitivity is improved by a factor of about 10-50. The added sensitivity allows the OPS 10 to operate at lower light, which reduces the power consumption. The light travels from the LED 14 through the finger to the blood vessel and tissue, where it is partially reflected. The reflected signal is sensed by the photodiode 16. This is the principle of reflectance photoplethysmography, which is a technique known per se.

By placing the LED 14 and photodiode 16 close together, the sensitivity improves, and the optimal sensing distance also becomes smaller. Typical optical proximity sensors have an optical sensing of 1-5 mm, which is the distance between the sensor and the blood vessel. The optical proximity sensor is compact, cheap, small, and integrates easily with digital microprocessors.

These technologies are integrated with a Bluetooth module 46 or another suitable wireless technology and with rechargeable batteries 32 in a small package, making the sensor assembly wireless and comfortably wearable throughout the day. OPS 10 and a low power Bluetooth transmitter can be integrated into the underside of a ring 44 or placed on a separate board 12' along with the battery 32. Beside Bluetooth technology and Bluetooth Low Energy technology, any other low-power transmission protocol is suitable for communication with a computer for evaluation.

This technology leads to a remarkably small (less than 50 mm², preferably less than about 25 mm²) and cheap (less than about $20) wireless heart rate sensor. The technology can be integrated into home health monitoring systems where the information is transmitted wirelessly to the patient's physician, hospital, and other caregivers, as schematically indicated in FIG. 11. It can also be incorporated into the patient's electronic medical record. The miniature, low cost wearable heart rate sensor has applications in various fields, such as remote patient monitoring (RPM).

As further shown in FIG. 11, a "cloud-based" RPM infrastructure can actively manage cardiovascular health. Using OPS technology, cardiovascular parameters can be monitored on a 24-hour ambulatory basis using wearable biosensors, with wireless transmission of relevant data to the patient's electronic medical record. These data will then be available to the patient's physician, providing an effective tool for quantitative assessment, without bias from "white-coat" alteration, thus providing a means for evidence-based medical management. In emergency situations, notifications can be sent to a medical response team and family members. An RPM-driven model will dramatically reduce the cost of chronic cardiovascular care through earlier detection of impending decompensation, white also improving health outcomes by motivating the patient to actively monitor health and take preventative measures.

Concept. One of several preferred embodiments of the invention involves a health ring 44 which can monitor heart rate on a 24 hour basis (FIG. 3C). The RPM models rely on continuous monitoring without placing burden to the patient. This proposal is based on a recent, unpublished discovery: OPS 10, traditionally used for position sensing, have an optical setup (FIG. 3D) well suited for photoplethysmography. More interesting, OPS 10 have an order of magnitude smaller size and power consumption than traditional photoplethysmography sensors. If successful, this novel sensing technology will lean to the smallest (less than about 50 mm2) and cheapest (no more than about $20) wireless heart rate sensor on the market—This device will assess heart rate (and potentially blood pressure) on a continual basis forming the foundation of an RPM platform that incorporates time-trending and variability assessment.

Having demonstrated that the sensor technology is fairly robust, a wireless ring 44 which combines the sensor with a Bluetooth, Bluetooth Low Energy (BLE), or other wireless transmitter linked to an application running on the user's cell phone.

The sensor and transmitter electronics can be arranged on a printed circuit board (PCB) using standard software. A mobile application may connect to the ring 44 via Bluetooth, downloads the photoplethysmography data, displays it on the screen, and uses signal processing to calculate the heart rate. Android is an open-source programming model with built-in libraries for simplifying the programming of Bluetooth and displays. Other operating systems and wireless protocols capable of communicating with a mobile device are also suitable. The ring 44 for slipping the sensor onto a finger may be made of injection molded plastics or cured elastomers, both of which are inexpensive, compatible with embedded electronics, and flexible to allow for multiple ring sizes.

The ring 44 serves as a housing for the sensor. The sensor includes electronics embedded into a plastic or rubber ring. As shown in FIG. 3C, the ring 44 is composed of two PCB boards 12 and 12', with interconnection provided by a flexible printed cable similar to those used cell phones. In one embodiment, the lower board 12 may contain the OPS 10, a Bluetooth system on a chip (BT-SOC) module, and a 2.4 GHz fractal antenna. The OPS 10 includes the optical barrier 28, LED 14, photodiode, ambient light detector, and electronic amplification/drive components which are controlled by an I²C interface. There may also be a transparent overlay between the sensor and the skin.

The lower board 12 may also include a galvanic skin response sensor. The Bluetooth SOC includes on-chip memory for storing up to 2 days of data, and a software stack which implements a standard Bluetooth client using a serial port profile. All parts on the lower board are expected to fit on an area approximately 1.7 cm by 1.7 cm, suitable for a ring monitor. The upper board, with approximately the same area, will contain 2 stacked lithium ion rechargeable batteries 32, which will provide up to 30 hours of continuous operation. The device will be encapsulated in a biocompatible low temperature cured elastomer or an injection molded plastic ring, tuned to a specific ring size. The ring could also be made of a rigid plastic.

The term optical proximity sensor in this context includes any optical proximity sensors, including light beam sensors, photointerruptors, multi-LED proximity sensors, multi-axis proximity sensors. These sensors have similar components or structures but may be referred to by different names. The term OPS is used in a broad sense to include all sensors that may use a different specific name, but that work in a similar way.

In another preferred embodiment, the upper board 12 contains the battery 32, battery charger, USB port for charging, a microprocessor 54 programmed with an operating system and the wireless module 46 including a microprocessor and an antenna 52 for communications. As illustrated in FIG. 12, this arrangement frees up space on the lower board 12' for the photodiode 16 or photodiodes 16, the LED 14, and the optical barriers 28. The lower board may thus additionally carry a temperature sensor 56 and the previously mentioned galvanic skin response sensor 58. The upper board 12 and the lower board 12' are connected via the flex cable 30 forming the ring shape of this wearable OPS 10.

In another example shown in FIG. 13, a miniature OPS device for an earlobe in the form of an ear clip 44 may have PCB boards on both sides of the earlobe. In the example of FIG. 13, the sensors are configured to be arranged on the underside of the earlobe, facing the earlobe. The wireless communication devices are arranged on the outside. The boards may, for example, be connected as shown with a clip 31 with embedded electrical connections. Alternatively, a post connected to one board may snap into a receiving socket connected to the other board. The latter solution provides a secure attachment of the sensor for individuals with pierced ears. Use of the ear as a sensor location may be preferred for minimizing motion artifacts though use of accelerometers and other motion correction measurements are possible. In addition to a clip the OPS sensors could be placed against the anterior auricular region or posterior auricular region instead of the lobe itself incorporated into a discrete accessory. Note the OPS sensor also could be integrated into multifunctional earpiece devices such as blue-tooth headsets.

In other variations of the arrangement, the sensor, memory chip, transmitter and antenna may be on one circuit board, while the battery and battery charger may be on the other. Thus, generally, the components can be arranged on the two circuit boards in various groupings. As previously mentioned, the battery 32 may be placed on the side of the earlobe opposite the OPS to improve the reflectance signal.

For providing a pulse wave velocity measurement over an extended vascular path, several sensors may be simultaneously placed in different locations of a patient's body along a circulatory path. These greater distances between measurement locations give useful information on the person's cardiovascular health by simultaneously measuring and comparing pulse delays, pulse shapes, or pulse strengths in the different locations. This practice enables measuring the pulse wave velocity in the path and not only at the location of one sensor.

Figure 8:
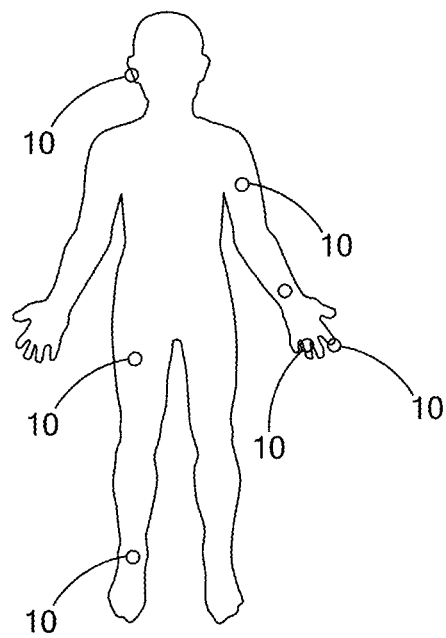
FIG. 8: Various examples of locations on a human body, in which optical proximity sensors may be placed for performing measurements.

FIG. 8 shows various options of such placements. For example, a first OPS 10 on an upper arm and a second OPS 10 on the same arm, but on the lower arm provides for subsequent measurements of the same pulse waves traveling through the arm arteries. Likewise, placement of the OPS 10 on an upper leg and a lower leg of the same leg allows for measuring the speed of a pulse through the leg arteries. A placement of OPS 10 on fingers and on an earlobe are also illustrated in FIG. 8

Two independent OPS 10 may be operating at different modulation frequencies or with alternating pulses. Both OPS signals can be processed by the same microprocessor to obtain real-time results. This approach is simpler than the sensor arrangement shown in FIG. 6A, but it consumes more power. Both approaches will keep the sensor size small (less than about 20% increase in the total area compared to a single-LED OPS).

Experiments show that the OPS 10 is relatively robust and can detect heart rate with in multiple anatomical locations. The OPS 10 itself has an approximate size of 4 mm by 4 mm, costing less than $4. In a preliminary study, the signal-to-noise ratio of the device consistently exceeded a factor of 50, indicating a sensitivity more than sufficient for detecting cardiac pulsation in the microcirculation.

Due to the low price, other potential markets may include consumer fitness (as replacement for straps, watches) and the mobile phone industry (as Bluetooth accessory). The worldwide market for home health monitoring of was worth about $10 billion in 2010

The conditions most commonly treated via these remote monitoring services include diabetes, cardiac arrhythmia, sleep apnea, asthma. More than 200 million people in Europe and the US suffer from one or more chronic conditions where remote monitoring would be helpful.

The proposed system can be used to monitor physiological activity and health on a continual basis. For example, the low-cost, hear rate sensor could be used to monitor sleep, exercise, and stress levels, enabling patient self-monitoring and driven decision making by health care providers. The key benefits to the proposed approach is 1) low cost, so it can be deployed to a large number of patients, ii) the sensor is small and nonintrusive, reducing patient discomfort and thereby increasing patient compliance, iii) it consumes low power, so it can provide 24 hour operation, iv) data is automatically transmitted wirelessly via Bluetooth, further reducing patient burden. The technology will result in new methods to assess efficacy and improve patient compliance to with physician-prescribed regimens.

The technology is suited to be deployed in a cloud-based health monitoring and mentoring framework which integrates remote patient monitoring (RPM) with an online community involving medical caregivers and a social network of the patient's peers. This framework may even be used to treat psychosocial disorders.

RPM provides quantitative, unbiased data which can be used for managing a wide range of chronic physiological and psychological disorders, including post-traumatic stress disorder, depression, hypertension, heart disease, sleep apnea, work stress, and many other psychosocial and physiological disorders. The small form factor and low power consumption of the proposed device is designed to provide all day use and be invisible, reducing patient burden.

Medical technology has increased the costs of healthcare over the last several decades. As a whole, remote patient telemonitoring is widely believed to be a critical step toward managing health care costs, while enhancing patient engagement and treatment compliance, an area of critical national priority given the rising costs of healthcare. Telemonitoring can reduce the total cost of care by reducing emergency and hospital visits, and unnecessary treatment, and is especially well suited for supporting patients with chronic conditions.

Heart rate variability and blood pressure are powerful indicators of physiological and psychological health, directly correlated to real-time emotional state and psychological resilience Sleep: Heart rate can be used to track sleep cycles, since both blood pressure and heart rate increase during REM sleep.

Exercise: Depressed patients report less physical activity than healthy individuals. Daily exercise can be monitored by increases in heart rate activity, similar to fitness monitors.

Stress: Both blood pressure and heart rate variability are closely linked to mental stress, providing a real time measure. Interestingly, heart rate variability is also an indicator of stress resiliency.

The OPS 10 was placed with fixed pressure in multiple locations, including the fingertip, an earlobe, and upper finger (to simulate a ring sensor). A metal backing was added to the OPS 10 on the opposite side of the earlobe to improve the reflectance signal. One example of an OPS formed as an ear clip 44 is shown in FIG. 13. Those elements that are placed on the board 12' of the battery 32 in FIG. 12 are placed on the outside of the ear clip 44 and face away from the person's head, shown in FIG. 13 on the right side. The battery 32 may additionally be arranged to provide a reflective surface for the light emitted by the LED 14 toward the photodiode 16. A button cell battery is well suited for this purpose due to its planar metallic end facing the LED 14 and the photodiode 16. The OPS 10 is placed on the inside of the ear clip 44, facing the earlobe from the side of the person's head. It is evident, that the locations may also be reversed without leaving the scope of the present invention.

Before performing the measurement, the current for the IR LED 14 must be set appropriately. It is advantageous to use a large current to maximize the reflected light. The signal-to-noise ratio is found to scale proportionally with the reflected light. However, too large a current will saturate the photodiode 16. The ideal current setting for the IR emitter lies between 80-130 mA, depending on the anatomical location, on the presence of a metallic reflector, and on the individual being tested. The IR emitter current can be set to autorange: in other words, the microcontroller can automatically tune down the emitter current if it saturates the photodiode, and increase the current if the reflected signal is low.

Figure 9:
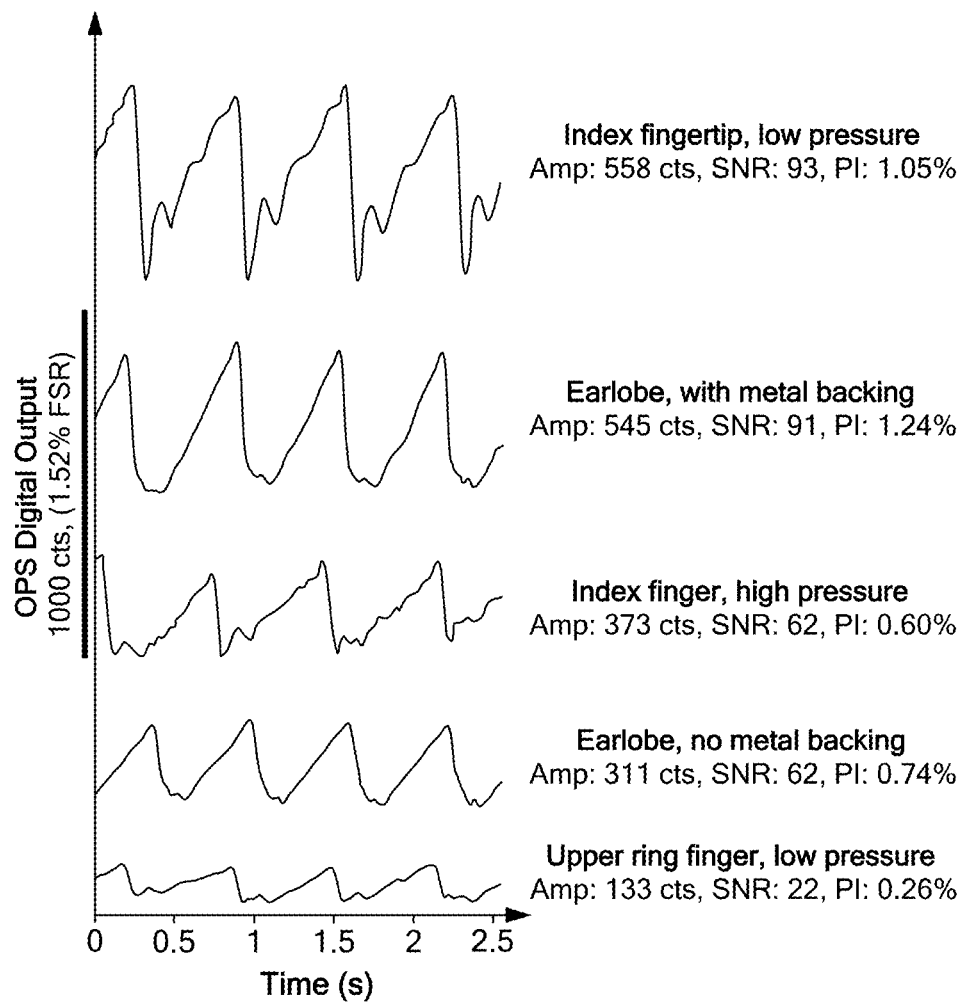
FIG. 9: Photoplethysmography waveforms from a single-LED OPS.

In summary, experiments show that the OPS 10 can produce high quality photoplethysmography measurements in multiple anatomical locations (FIGS. 5 and 9). The signal-to-noise ratio of the photoplethysmography signal typically varies between 20-90 depending on the location and the applied pressure. This is comparable to or better than the values obtained using existing photoplethysmography sensors (~30-50), and is sufficient for detecting cardiac pulsation in the microcirculation. Typical pulsation indices (PI) vary from 0.26-1.25%, which is typical for reflectance pulse oximetry, and is well within the resolution of the 16 bit ADC. As indicated above, the power consumption of the device is less than about 200 µW at a 100 Hz data rate. This is 7 times smaller than the state of the art, and more than about 10 times smaller than commercial devices. The size is more than about 10 times smaller than the state of the art. These qualities make the sensor well-suited for wearable monitors. Heart rate is easily calculated from resultant waveforms using computationally inexpensive signal processing algorithms based on the time derivatives of the photoplethysmography signal, infinite impulse response, averaging windows, or other approaches.

Table 1 compares the performance of the digital OPS 10 with existing state-of-the art photoplethysmography sensors in both the research and commercial sectors. It is notable that the OPS-based photoplethysmography provides better performance in most categories, including those of particular interest in wearable sensors. These advantages include a substantial reduction in power (about 5 times), size (about 10 times), and cost (about 5-10 times), along with a significant improvement in signal-to-noise ratio by a factor of about 2 to 3. Most importantly, the sensor provides a plug-and-play solution with a digital output on an industry standard $I_2C$ interface, making it simple to integrate a high performance photoplethysmography sensor into an embedded device.

TABLE 1

Comparison of Optical Proximity Sensor with conventional photoplethysmography (PPG) sensor

| Performance Parameter | Existing PPGs (best case) | OPS-based PPG |
| --- | --- | --- |
| # of Components | >10 | 1 |
| PCB Area | 200 mm² | 16 mm² |
| Power Consumption | 1.5 mW-10 mW | 0.2 mW (100 mA, 10 Hz) |
| Cost: | $10-20 | $2 |
| Supply Voltage | 3 V/5 V | 3 V |
| Sensor Output | Analog | Digital (I²C serial) |
| Maximum data rate | 200 Hz | 1000 Hz |
| Measurement time | 1.25 ms | 76 µs |
| LED drive current |  | 10-200 mA |
| LED, PD spacing | 4-6 mm | 1-2 mm |
| Optical sensing distance |  | 2-10 mm |
| Noise rejection features | Bandpass filter: 0.5-5 Hz | Electronic ambient light cancellation @3.125 MHz Flicker: 100/120 Hz |
| IR filter | Not included | Integrated |
| signal-to-noise ratio | 20-30 | Up to 95 |
| Wavelength | 650-950 nm | 895 nm (can be changed) |

Some OPS sensors do not require that the LED emitters are included on the chip 48. Other types of proximity sensors (for example, the Silicon Labs 1114X series) include a photodiode, drivers, and signal processing electronics, but does not include an LED. The LEDs can be placed remote from the electronics. This allows positioning the LEDs any place possible, with or without an optical barrier 28. The LEDs could even be placed on the opposite side of the tissue, for instance on the other side of an earlobe of finger, enabling a transmission-mode photoplethysmography.

Figure 15:
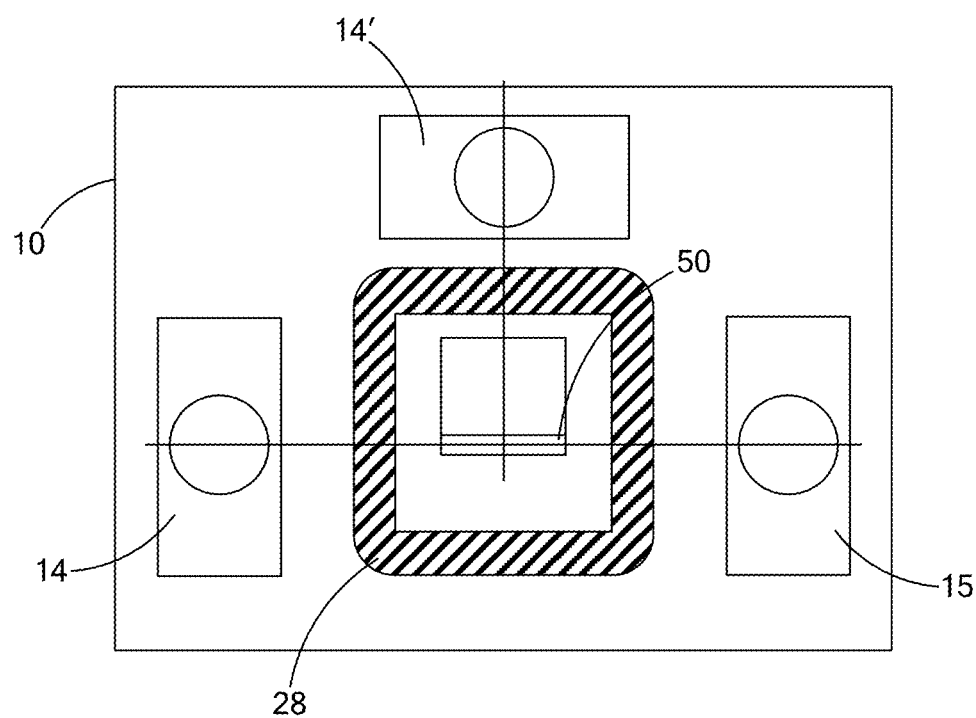
FIG. 15: A schematic of a proposed sensor system for pulse oximetry monitoring with three LEDs, one photo detector containing different photodiodes, and two optical barriers.

In yet a further development, a compact OPS 10 may contain a plurality of LEDs that may each emit light in a different spectral range (FIGS. 14 and 15). A photo detector equipped with different photodiodes 16 and 20 tuned to the emitted wavelengths can distinguish the individual reflected photons by their wavelength. For example, if one LED 15 emits red light and a second LED 14 emits light in the near infrared, a pulse oximetry sensor can be realized with a very small size. FIG. 14 illustrates how one red LED 15 and one IR LED 14 are arranged on opposite sides of a photo detector 50 that includes photodiodes 16 and 20 sensitive to different spectral ranges, here red for photodiode 20 and near IR for photodiode 16. Each of the LEDs 14 and 15 is separated from the photo detector by an optical barrier 28. The optical barriers 28 do not touch the transparent cover 29 that separates the LEDS 14 and 15, the optical barriers 28, and the photo detector 50 from the human skin because a direct contact between the optical barrier 28 and the cover 29 might result in a bad signal quality. The height of the optical barriers 28 may be derived from empirical measurements until an optimum configuration is found. The arrangement of FIG. 14 further shows copper barriers 60 embedded in circuit board 12' extending from underneath each of the LEDs 14 and 15 to a location underneath the adjacent optical barrier 28, respectively, to avoid a light leakage through the circuit board 12' from the LEDs 14 and 15 to the photodiodes 16 and 20.

Pulse oximetry measures blood oxygenation ($SpO_2$) by comparing the pulsation indices at two wavelengths with known absorbance characteristics in oxygenated vs. deoxygenated blood. A multi-LED digital OPS 10 can provide multiple photoplethysmography waveforms, each with a different LED, and can therefore obtain radiometric measurements required for pulse oximetry.

FIG. 15 shows an alternative arrangement, in which the LEDs are arranged in the same sensor assembly, but separate from the circuit board, on which the photo detector 50 is mounted. This arrangement may require more space, but can still be accommodated in an area of less than 1 cm². Several LEDs may be placed in an orthogonal arrangement The use of a multi-LED OPS 10 for pulse oximetry is shown schematically in FIGS. 14, 15, 16, and 17. The multi-LED OPS 10 detects signals from multiple discrete LEDs 14 and 15, and optionally 14', which can be multiplexed on a single photo detector 50 equipped with photodiodes 16 of infrared detection and photodiodes 20 for detecting red light. A typical sensor shown in 17 includes the photo detector 50, 2 or more LED drivers, and electronics for signal conditioning and multiplexing the data channels on a common circuit board 48. The LEDs 14 and 15, and optionally 14', are added separately to the circuit board, along with an optical barrier 28 to reduce leakage if desired as shown in 15. While this increases the chip count, it does allow flexibility in positioning the LEDs 14 and 15, and 14' for either transmittance or reflectance mode, and in choosing the appropriate wavelengths.

For pulse oximetry, a minimum of two LEDs 14 and 15 is required, typically in the 650-950 nm range, with one LED 14 emitting in the near IR and the other LED 15 emitting in the red spectral range as illustrated in FIG. 14. A wide spectral sensitivity in the photo detector 50 is preferable. Alternatively, two photodiodes may be used with different spectral sensitivity ranges.

The measurements from the two LEDs 14 and 15 can be time multiplexed or frequency multiplexed. In the former case, each LED is modulated at a unique frequency, and reflectance signal from each LED can be extracted using on-chip demodulators. In time multiplexing, the LED measurements are interleaved. In both modes, frequency modulation can be used to improve noise reduction. Once the pulsation indices from the two channels have been extracted, their ratio can then be used to determine the SpO2 in the capillary bed.

Thus, suitable wavelengths for pulse oximetry are in the range of about 600 nm to 700 nm for the red LED 15, preferably between about 650 nm and 670 nm, and about 850 nm to 950 nm, preferably about 900 nm to 940 nm for the near infrared LED 14. Notably, a deviation from the preferred wavelengths is feasible and may make the sensor 10 cheaper due to the availability of commercially produced LEDs 14 and 15. The two LEDs 14 and 15 may be pulsed. Optionally, the two LEDs 14 and 15 may be pulsed at different frequencies through frequency multiplexing. Alternatively. The LEDs 14 and 15 may be pulsed in an alternating mode through time multiplexing. Pulsing the LEDs 14 and 15 promotes an easy distinction of the two signals where both signals are received by the same photo detector.

Figure 18:
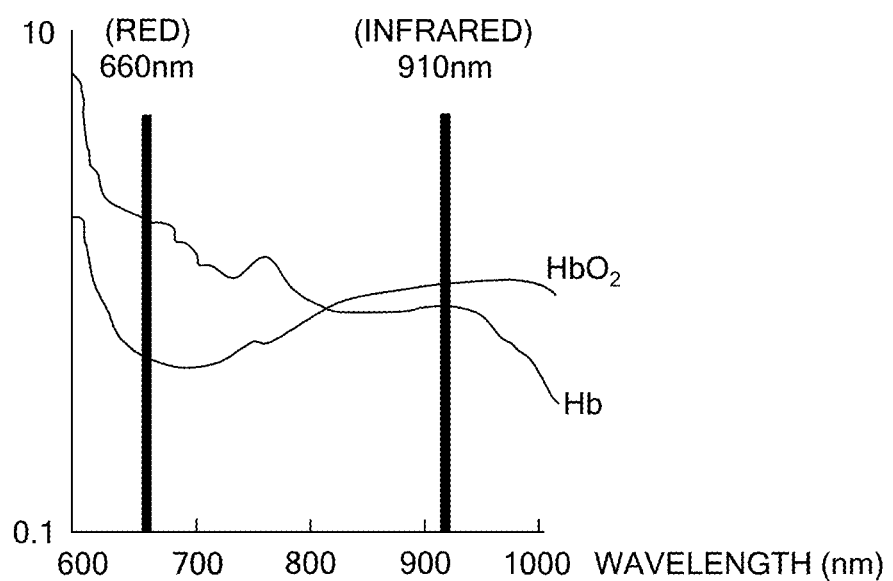
FIG. 18: A diagram depicting light absorption of oxyhemoglobin and reduced hemoglobin.

FIG. 18 illustrates the absorption spectra of oxyhemoglobin, i.e. hemoglobin that has been enriched with oxygen and is found in arterial blood, and of reduced hemoglobin, i.e. hemoglobin that does not carry oxygen. Because Oxyhemoglobin is typically found in arteries, pulse oximetry measures the component of the reflected infrared signal that alternates with the pulse of a patient. The red signal, on the other hand, is much more indicative of the reduced hemoglobin, which is more prevalent in veins and should thus not show a strong pulse. The red LED 15 thus gives a baseline measurement. Comparing the signals from the two LEDs 14 and 15 allows one to measure blood oxygenation, also referred to as SPO2, or oxygen partial pressure.

The details of pulse oximetry are known in the art and need not be explained in detail.

A suitable concept that allows to build such a compact sensor 10 can, for instance, be based on small-scale motion sensors that include two or more LEDs 14 and Á. While those motion sensors typically include LEDs of the same color, the LEDs can be chosen to emit light in different colors. The photo detectors of these sensor systems typically include photodiodes 20 that are sensitive to the visible spectrum and other photodiodes 16 sensitive to the near infrared spectrum. The photodiodes 20 sensitive to the visible spectrum typically serve to determine the amount of ambient light, but can also be used to detect reflected light from the red LEDs 14 and 14'.

Figure 19:
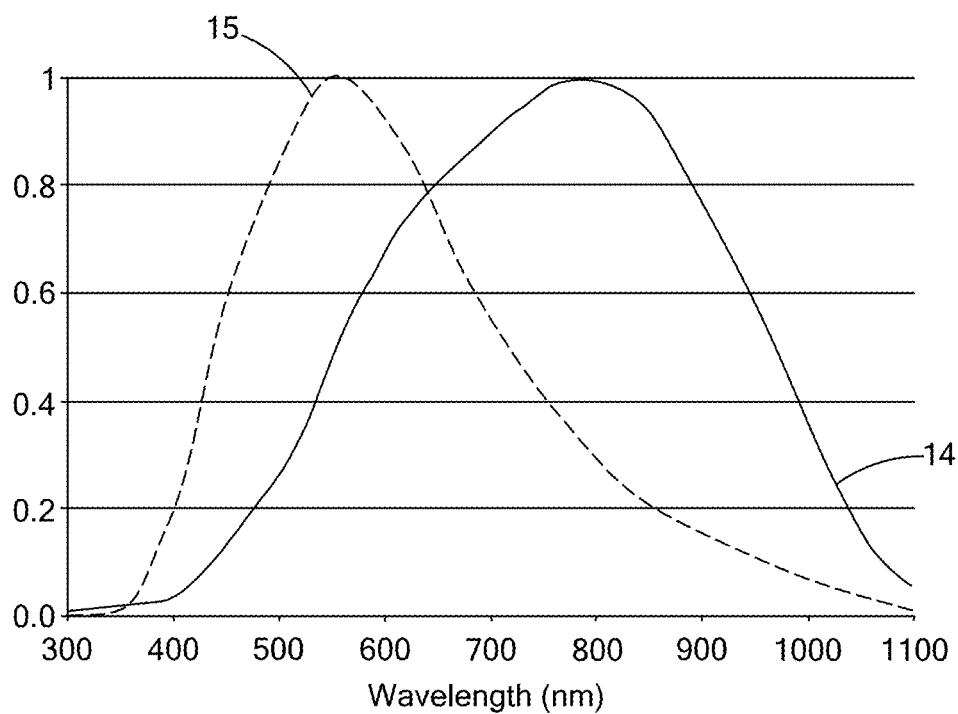
FIG. 19: A diagram depicting light sensitivity of different photodiodes in the visible and near infrared spectrum.

FIG. 19 shows the normalized sensitivities of two photodiodes 20 and 16, one for the visible spectrum and one for the near infrared spectrum. The sensitivities overlap so that the diode for the visible spectrum will also sense near infrared light and vice versa. Proper calibrations can compensate this disturbance with algorithms reducing the component of the respective other light source. Calibration measurements can be performed periodically or sporadically by individually taking measurements without any LED light, with one LED light operating, and with the other LED light operating.

Figure 17:
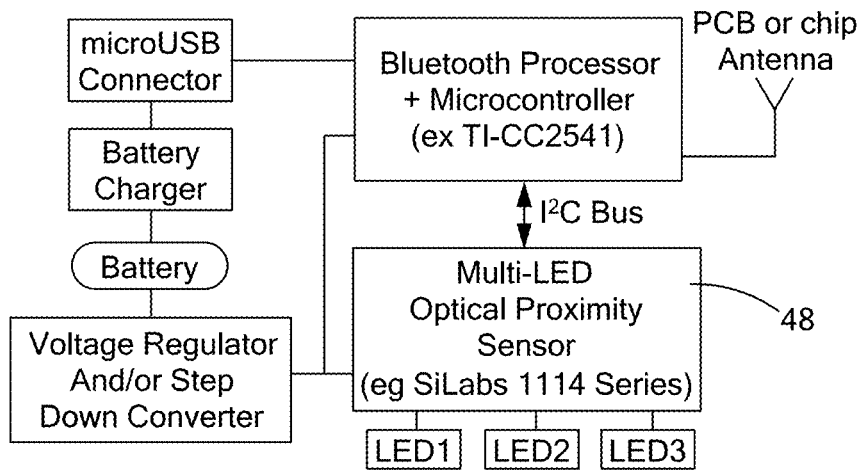
FIG. 17: An example of a circuitry of a pulse oximetry sensor according to the invention.

For pulse oximetry, the Silicon Labs Si1143 was used, a triple-LED digital OPS 10, as is schematically indicated in FIG. 17. The chip 48 includes a photodiode 50 with FWHM spectral bandwidth of 600-1000 nm, 3 LED drivers, and a signal conditioning logic on the embedded IC. Unlike the VCNL4000, the Si1143 does not include the LEDs on the chip 48 itself. Surface mount IR LEDs 14, 14', and 15 (OSRAM) were placed within 3 mm on either side of the photodiode. The half angle of the chosen LEDs 14, 14', and 15 is 22 degrees, which limits the light leakage. Each LED current can be set between 5.6 and 360 mA. The Si1143 uses time multiplexing to measure the reflectance from two or three LEDs on a single photo detector. Like the VCNL4000, it uses short LED pulses (25 µsec), which reduces the power consumption of the system. With three 100 mA LEDs 14, 14', and 15 operating at a 100 Hz data rate, the power consumption is still less than about 800 µW. The Si1143 also includes an I²C bus interface 26 for sensor configuration and reading sensor data. The ambient light sensor 20 included on the chip 48 can be used for sensing whether the chip 48 has been placed in contact with the skin.

Figure 16:
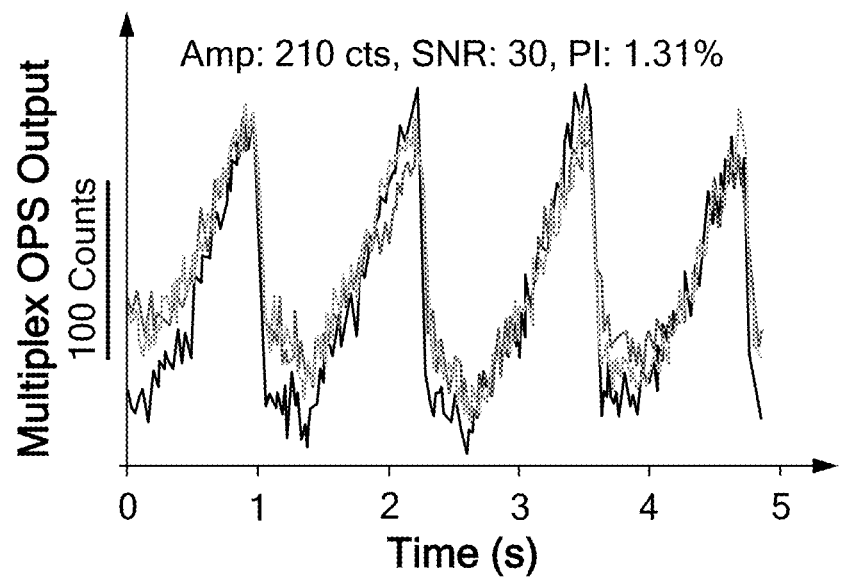
FIG. 16: Three photoplethysmography waveforms measured simultaneously on the index fingertip with the Multi-LED OPS of FIG. 12.

Results from the Multi-LED are shown in FIG. 16. This experiment used three LEDs 14, 14', and 15 placed 3 mm from a photo detector 50 formed by a Si1143 sensor as indicated in FIG. 15. A single measurement was taken at the fingertip at a fixed, moderate pressure. The three simultaneous photoplethysmography waveforms are shown in the same graph. The signal-to-noise ratio is somewhat lower than similar measurements taken with the VCNL4000, but this is likely due to the smaller LED current used (30 mA vs. 100 mA). The pulsation index is slightly larger, which may be due to the placement or emission characteristics of the LEDs. The $SPO_2$ measurement can be found by taking the ratio of amplitudes in two LED channels. This calculation is performed by a microcontroller (not shown).

The measurement protocol for the Si1143 is identical to the single-LED experiment.

Although commercially available VCNL4000 and Si1143 sensors were used for the OPS 10, this technique can be used with any suitable digital OPS 10, reflective light sensor, photo interrupter, or similar component. Examples include (but are not limited to) the OSRAM 770/773, the Avago APDS-9190, and the Intersil ISL29011/21/27/28. Examples of Multi-LED optical proximity sensors include the Rohm BH1771GLC, as well as the Si1141/42/43 series.

While the schematic setup shown in FIG. 17 for operating a pulse oximetry sensor according to the present invention depicts three LEDs 14, 14', and 15, two LEDs, for example LED 14 and LED 15, are sufficient for performing the required measurements as discussed above.

It is known that certain factors may render pulse oximetry unreliable because the presence of other components (e.g. methemoglobin or carboxyhemoglobin) in the blood may mimic the absorption of oxyhemoglobin at the IR LED frequency so that the reading is falsified. Such errors can be minimized by adding a third LED emitting light of a wavelength at which the component shows a different behavior than oxyhemoglobin and reduced hemoglobin. FIG. 15 shows an arrangement of the three LEDs 14, 14', and 15, positioned on three sides of a photo detector in the form of photodiode 50. An optical barrier 28 separates the photo detector from all three LEDs 14, 14', and 15. The three LEDs 14, 14', and 15 may all emit different wavelengths. LEDs 15, and 14, for example, may emit light in the red and IR spectrum, respectively, while LED 14' may emit light at a wavelength at which the presence of falsifying components can be detected. The photo detector 50 includes photodiodes sensitive to all three wavelengths.

In summary, OPS 10 have traditionally been used in robotics and smart phones, but here we show that OPS 10 perform all photoplethysmography functions in a single, 4 mm-by-4 mm package which links directly to a microcontroller via a standard serial interface. Moreover, it provides substantial performance advantages over existing state-of-the-art photoplethysmography sensors, including: i) 10 times lower power consumption (200 µW), ii) 5 times lower cost ($4), iii) 20 times smaller area, and iv) High signal-to-noise ratio (more than about 90), as a result of built-in optical barriers 28, filters, and ambient light cancellation. The versatility of the device can be demonstrated by measuring photoplethysmography data in several anatomical locations. A multi-LED OPS 10 can provide dual wavelength measurements required for pulse oximetry. These unique qualities make OPS 10 an elegant solution for battery-powered, wearable physiological monitors.

It has been shown that digital optical proximity sensors (OPS) can provide high quality photoplethysmography measurements in a 4 mm-by-4 mm package and with power consumption less than about 200 µW. This order of magnitude improvement, along with size and cost benefits, suggests that OPS are well suited for miniature wearable photoplethysmography sensors for continuous health monitoring.

While the present invention has been described in terms of preferred embodiments, it will be understood, of course, that the invention is not limited thereto since modifications may be made to those skilled in the art, particularly in light of the foregoing teachings.

The invention claimed is:

1. An optical proximity sensor assembly for cardiovascular monitoring, the optical proximity sensor assembly comprising:
   an optical proximity sensor having
      a first IR LED emitting light having an infrared wavelength;
      a first IR photo detector sensitive to the infrared wavelength; and
      an electronic integrated circuit with an amplifier for amplifying a signal detected by the first IR photo detector, an analog to digital converter, LED drivers, noise reduction and ambient light cancellation circuitry, and a digital interface for communication with a microcontroller; and
   a wearable carrier accommodating the optical proximity sensor and configured for placing the optical proximity sensor in contact with skin;
   wherein the wearable carrier is a clip wearable on an earlobe, the clip including the first IR LED and the first IR photo detector in a first portion of the clip to be placed on a first side of the earlobe and a metallic reflector in a second portion of the clip to be placed on a second side of the earlobe opposite the first side, the metallic reflector being arranged to reflect the light emitted by the first IR LED toward the first IR photo detector; and
   wherein the clip includes a battery disposed in the second portion of the clip, wherein the battery has a reflective surface facing the first IR LED and the first IR photo detector that provides the metallic reflector.

2. The optical proximity sensor assembly of claim 1, wherein the optical proximity sensor further comprises a transparent cover covering the first IR LED and the first IR photo detector.

3. The optical proximity sensor assembly of claim 1, further comprising an optical barrier between the first IR LED and the first IR photo detector, the optical barrier blocking direct light rays from the first IR LED to the first IR photo detector and permitting reflected light rays to reach the first IR photo detector.

4. The optical proximity sensor assembly of claim 1, wherein the analog-to-digital converter has at least a 12-bit resolution.

5. The optical proximity sensor assembly of claim 1, further comprising a wireless transmission system and an electronic processor with an operating system compatible with a remote wireless device.

6. The optical proximity sensor assembly of claim 1, wherein the optical proximity sensor further comprises a visible light blocking filter shielding the first IR photo detector.

7. The optical proximity sensor assembly of claim 1, wherein the battery has a capacity sufficient to operate the optical proximity sensor assembly for at least 24 hours.

8. The optical proximity sensor assembly of claim 1, wherein the first IR LED is pulsed.

9. The optical proximity sensor assembly of claim 8, wherein the first IR LED is configured to operate in a low-duty-cycle mode by burst operation.

10. The optical proximity sensor assembly of claim 8, wherein the first IR LED is pulsed at a frequency of at least 100 Hz.

11. The optical proximity sensor assembly of claim 8, wherein the first IR LED is pulsed at a frequency of at least 1 kHz.

12. The optical proximity sensor assembly of claim 8, wherein the first IR LED is pulsed with a pulse width of at most 100 µs.

13. The optical proximity sensor assembly of claim 1, wherein the first IR LED, the first IR photo detector and other components of the optical proximity sensor assembly are arranged on two circuit boards.

14. The optical proximity sensor assembly of claim 13, wherein at least the first IR LED and the first IR photo detector are arranged in a package covering an area of at most 1 cm$^2$.

15. The optical proximity sensor assembly of claim 14, wherein the area is at most 20 mm$^2$.

16. The optical proximity sensor assembly of claim 15, wherein the area is at most 17 mm$^2$.

17. The optical proximity sensor assembly of claim 15, wherein a first electronic board and a second electronic board are arranged on the clip, the clip forming electric conduits connecting the first and second electronic boards.

18. The optical proximity sensor assembly of claim 1, further comprising a second LED.

19. The optical proximity sensor assembly of claim 18, wherein the first IR LED and the second LED are pulsed at a different frequencies so as to enable frequency multiplexing.

20. The optical proximity sensor assembly of claim 18, wherein the first IR LED and the second LED are pulsed in an alternating order so as to enable time multiplexing.

21. The optical proximity sensor assembly of claim 18, wherein the second LED emits red light.

22. The optical proximity sensor assembly of claim 21, wherein the first IR photo detector is also sensitive to the red light emitted by the second LED.

* * * * *